(12) United States Patent
Mariella, Jr.

(10) Patent No.: US 6,787,104 B1
(45) Date of Patent: Sep. 7, 2004

(54) DETECTION AND TREATMENT OF CHEMICAL WEAPONS AND/OR BIOLOGICAL PATHOGENS

(75) Inventor: Raymond P. Mariella, Jr., Danville, CA (US)

(73) Assignee: The Regents of the University of California, Oakland, CA (US)

( * ) Notice: Subject to any disclaimer, the term of this patent is extended or adjusted under 35 U.S.C. 154(b) by 140 days.

(21) Appl. No.: 09/662,392

(22) Filed: Sep. 14, 2000

(51) Int. Cl.[7] ............................ A61L 9/00; B60H 3/00; B08B 3/00; C12M 1/36; A62D 3/00
(52) U.S. Cl. ............................... 422/4; 422/1; 422/62; 422/124; 454/156; 454/157; 454/255; 454/256; 134/198; 435/286.1; 435/287.4; 588/200
(58) Field of Search .......................... 422/1, 4, 62, 124; 134/198; 454/156–157, 255–256; 588/200; 435/286.1, 287.4

(56) References Cited

U.S. PATENT DOCUMENTS

| | | | | |
|---|---|---|---|---|
| 4,022,876 A | * | 5/1977 | Anbar | 424/1 |
| 4,140,005 A | | 2/1979 | Kittelson | 73/28 |
| 5,074,137 A | * | 12/1991 | Harris et al. | 73/31.02 |
| 5,078,046 A | * | 1/1992 | Mascolo et al. | 454/157 |
| 5,766,956 A | * | 6/1998 | Groger et al. | 436/164 |
| 5,938,823 A | * | 8/1999 | Condit et al. | 96/16 |
| 6,293,861 B1 | * | 9/2001 | Berry | 454/255 |
| 6,296,808 B1 | * | 10/2001 | Pearman | 422/62 |
| 6,375,697 B2 | * | 4/2002 | Davies | 55/340 |

FOREIGN PATENT DOCUMENTS

WO  WO 98/58743  12/1998

OTHER PUBLICATIONS

Begrader et al., "Autonomous System for Pathogen Detection and Identification," Sep. 24, 1998, (11 pages), Lawrence Livermore National Laboratory.*
Belgrader, P., et al., "Autonomous System for Pathogen Detection and Identification," Sep. 24, 1998, UCR-L–JC–128919 Preprint, (11 pages), Lawrence Livermore National Laboratory, prepared for Society of Photo–Optical Instrumentation Engineers International Symposium on Industrial and Environmental Monitors and Biosensors in Boston, MA Nov. 1–6, 1998.
Mariella, R., "Biomedical Instrumentation Based on Micro– and Nanotechnology," Jan. 24–25, 2001, Progress in Biomedical Optics and Imaging, vol. 2, No. 22, (8 pages) Proceedings of SPIE, vol. 4265.
Ferrari, M., "Micro– and Nanofabricated Structures and Devices for Biomedical Environmental Applications II," Jan. 25–26, 1999, Progress in Biomedical Optics, (8 pages), SPIE Proceedings Series, vol. 3606.
Mariella, R., "Microtechnology for Instrumentation," Jan. 1998, UCRL–JC–129215 Preprint, (10 pages), Lawrence Livermore National Laboratory, prepared for Society of Photo–Optical Instrumentation Engineers Photonics West Meeting, San Jose, CA Jan. 26–28, 1998.

* cited by examiner

Primary Examiner—Jill Warden
Assistant Examiner—Monzer R. Chorbaji
(74) Attorney, Agent, or Firm—Eddie E. Scott; Alan H. Thompson (57) ABSTRACT

A system for detection and treatment of chemical weapons and/or biological pathogens uses a detector system, an electrostatic precipitator or scrubber, a circulation system, and a control. The precipitator or scrubber is activated in response to a signal from the detector upon the detection of chemical weapons and/or biological pathogens.

11 Claims, 4 Drawing Sheets

DETECTION AND TREATMENT OF CHEMICAL WEAPONS AND/OR BIOLOGICAL PATHOGENS

The United States Government has rights in this invention pursuant to Contract No. W-7405ENG-48 between the United States Department of Energy and the University of California for the operation of Lawrence Livermore National Laboratory.

BACKGROUND OF THE INVENTION

1. Field of Endeavor

The present invention relates to the detection and treatment of chemical and biological agents, and more particularly, to a system for protecting a building or other enclosed airspace from harmful aerosol particles.

2. State of Technology

Biological agent weapons have been around at least since the Middle Ages when soldiers are reported to have catapulted the bodies of dead smallpox or plague victims over fortress walls in the hope of infecting their enemies or at least demoralizing them. Today, biological weapons (BW) are appearing in the news with increasing frequency. The anthrax threat in Las Vegas in February 1998 is an example. Surplus stores in Las Vegas sold out of gas masks, and talk-radio shows were swamped with callers asking about evacuation points. That threat turned out to be a false alarm, but the next one might be real. The Aum Shinrikyo cult grew and released anthrax spores in Tokyo, but, fortunately they did not have and effective means of dispersal of the spores and no deaths were reported. In Sverdlovisk, Union of Soviet Socialistic Republics in 1979 a quantity of dry anthrax spores were accidentally released from a military facility, killing 67 people downwind.

Biological agents are of concern in part because of the ease with which many of them can be manufactured, transported, and dispensed. Because of the lag time between a biological attack and the appearance of symptoms in those exposed, biological weapons could be devastating. Many biological agents are contagious; and during this lag time, infected persons could continue to spread the disease, further increasing its reach. Hundreds or even thousands of people could become sick or die if a biological attack were to occur in a major metropolitan area.

A historical example illustrates the scale of the effort required to respond to an act of BW terror in a major metropolitan area. In 1947, an American businessman traveled to New York City from Mexico City. During his bus ride, he developed a fever, headache, and rash. Though ill upon his arrival in New York, he went sightseeing. Over a period of several hours, he walked around the city and through a major department store. His illness, smallpox, progressed and he died nine days later. As a result of this single case, other cases of smallpox and two deaths occurred. Because of smallpox's ability to be transmitted from person to person, this handful of cases was deemed so serious by public health officials that 6,350,000 persons in New York City alone were vaccinated in less than a month.

In view of the foregoing, there is an increasing need for a system for detecting and eliminating biological and chemical agents. The system could be installed in a building or other area with an enclosed airspace. For example the system could be installed in subways, airports, entertainment centers, religious centers, office complexes, convention centers, and other sites where the public is at high risk of exposure to a covert release of biological or chemical agents. The system could also be part of a network of systems installed in urban areas or large events such as inaugurations or the Olympics.

The majority of detection and identification systems that are currently commercially available generally require a laboratory setting for testing and are designed for one positive detection only (Military System). There is also the question "what would be recommended as an action, if a real pathogen were detected?" Most people do not have a HEPA-filtered mask available. Even if a HEPA-filtered mask were available, it would likely not be properly fitted; and the individual would likely not be properly trained for its use.

The present invention provides a prophylactic approach that can avoid many of the problems of the prior art by providing monitoring and remediation of the entire air supply. The prior art systems are piecemeal systems that do not provide an entire solution to the problem. For example, the system described in The World Intellectual Property Organization International Patent Application No. WO 98/58743 to Patricia Irving and Donald Hammerstrom, assigned to Coma Catalysis Corporation and Battelle Memorial Institute, filed Jun. 16, 1998, an electrostatic precipitator capable of separating Am size particulate matter for a gaseous stream is described. Alternating plates and ground collector plates are placed in a particulate laden gas stream. The collector plates are provided with a plurality of micromachined channels therein aligned generally perpendicular to the flow of gas through the device. The channels are provided with a liquid flowing therethrough to collect and concentrate the particulates collected therein. Analytical means may be provided to analyze the particulate matter thus collected.

U.S. Pat. No. 4,140,005 to David B. Kittelson, assigned to The Regents of the University of Minnesota, filed Feb. 20, 1979, and issued Mar. 22, 1977, describes a method and instrument for continuous monitoring of an aerosol as the sulfur content of atmospheric aerosols. The instrument has an electrostatic precipitator that is turned off and on at a given frequency to modulate the particle concentration of aerosol flowing through the precipitator. A total sulfur flame photometric detector sensitive to both gaseous and particulate sulfur receives a sample of the modulated aerosol from the precipitator. The modulated particle concentration of the aerosol supplied to the detector causes a fluctuating component in the detector output that is directly related to the sulfur particle concentration. This component is amplified by a frequency and phase sensitive lock-in amplifier tuned to the precipitator modulation frequency. The resulting output signal gives a continuous measure of the sulfur particle concentration entering the instrument. Because this system is designed to have its electrical power turned off half of the time, it is clearly designed for detection, not protection of building's occupants.

U.S. Pat. No. 5,938,823 to David A. Condit, Timothy N. Obee, Willard H. Sutton, Richard R. Grzybowski, Christopher M. Pater, Antonio Rinaldi, Sunita Satyapal, Wayde R. Schmidt, Charles R. Winston, and Michael Winter, assigned to Carrier Corporation, filed Apr. 18,1997, and issued Aug. 17, 1999, describes an air cleansing apparatus including an electrostatic precipitator in which the collector plates are made of, for instance, reticulated chemical vapor deposited silicon carbide, or reticulated silicon carbide ceramic coated with titanium nitride, zirconium diboride, or chemical vapor deposited silicon carbide. Microorganisms entrained on the collector plates are thermally degraded or vaporized by microwave radiation directed against the plates during a sterilization period which follows a collection period.

BRIEF SUMMARY OF THE INVENTION

The present invention provides an autonomous chemical and pathogen detection and remediation system. It provides a system for the detection and treatment of unwanted agents within the air inside of an enclosed airspace that is a gathering area for people. The air is channeled into an air stream. A detector system is located within the air stream for detecting the unwanted agents. An electrostatic precipitator and/or "scrubber" is connected to the air stream. A circulation system is provided for moving air within the air stream. A control is connected to the detector, the circulation system, and the electrostatic precipitator/scrubber to activate the electrostatic precipitator/scrubber in response to detection of unwanted agents.

This system can be used to monitor and remediate circulating air inside of an enclosed airspace. Specific examples of areas that need protection are subways, airports, entertainment centers, religious centers, office complexes, convention centers, and other sites where the public is at high risk of exposure to a covert release of biological or chemical agents. The system could be used for the detection and treatment of chemical and biological agents in the event a terrorist were to release an aerosolized agent into the airspace or the ventilation system. The present invention provides a prophylactic approach that can avoid many of the problems of the prior art by providing remediation of the entire air supply.

Implementation of the present invention would have a deterrent effect. The complete vulnerability of public areas such as subways, airports, entertainment centers, religious centers, office complexes, convention centers to terrorism prompt other terrorists to attempt the same type of attack for extortion or additional terror impact. The existence of the building protection system of the present invention would provide a deterrent to this type of extortion.

Another important use of the building protection system is that it can be used to provide a safe haven in the event of a terrorist BW attack. A BW agent terrorist attack could be dealt with to some degree, if buildings is equipped with the system described and claimed in this patent application. People would be advise to stay inside the building, equipped with the system described and claimed in this patent application, while the cloud of BW agent dispersed. The occupants of the building would be protected until the main cloud of BW agent passed.

There are other uses of the present invention. Air monitoring is of critical importance to public health assessment. There needs to be a system capable of providing a warning of a high level of airborne particulates and treatment of the dangerous particulates. For example, recirculation of air in buildings as indoor pollution causes worker illness. Unwanted particles accumulate in the recirculated air. Nosocomial, or hospital-acquired infections are often caused by antibiotic resistant microorganisms spread throughout the hospital in air-handling systems. The infections are also in the ambient air caused by movement between rooms by hospital personnel. The present invention provides an autonomous chemical and pathogen detection and remediation system that will diminish or eliminate these problems.

Additional aspects, advantages, and features of the invention are set forth in part in the following description. Various aspects, advantages, and features of the invention will become apparent to those skilled in the art upon examination of the description and by practice of the invention.

DETAILED DESCRIPTION OF THE INVENTION

There is an increasing need for a system for detecting and treating biological and chemical warfare agents. The threat of an attack with chemical or biological weapons on U.S. citizens is a high priority concern. Events such as the World Trade Center and Oklahoma City bombings, the Tokyo subway nerve gas attack, the Sverdlovisk Soviet Union release of dry anthrax spores, and several bio-terrorism scares have accelerated private and U.S. Government efforts to combat terrorism, particularly chemical and biological terrorism. In the face of the potential for chemical and biological terrorism, the country's national security is increasingly defined by its ability to respond with new technology. Biological warfare is the intentional use of micro-organisms and toxins, generally, of microbial, plant, or animal origin to produce disease and/or death in humans. This can be accomplished directly, through the food supply, through the water supply, or through the air supply. Biological agents are of particular concern because of the ease with which they can be manufactured, transported, and dispensed. Because of the lag time between a biological attack and the appearance of symptoms in those exposed, biological weapons could be devastating. Many biological agents are contagious; and during this lag time, infected persons could continue to spread the disease, further increasing its reach. Hundreds or even thousands of people could become sick or die if a biological attack were to occur in a major metropolitan area. Because the lethality of an airborne pathogen depends upon its concentration, the greatest threat to our citizens would be the release of a quantity of agent into an enclosed airspace of an occupied building.

Figure 1:
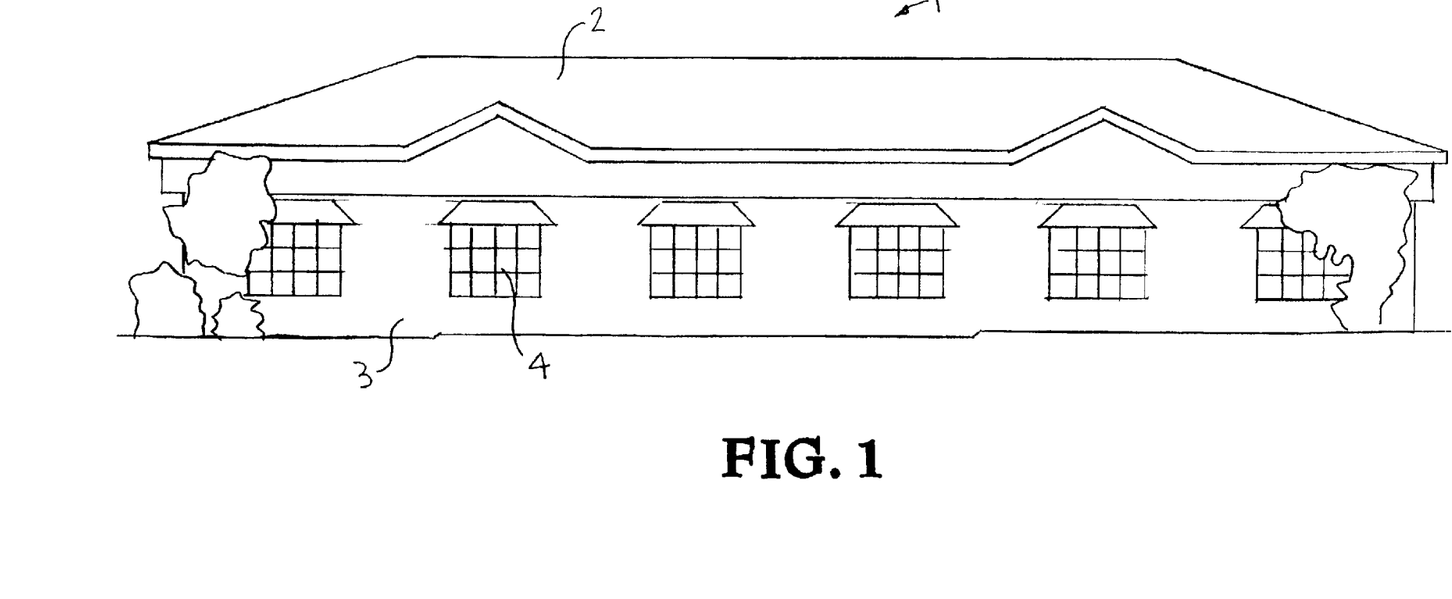
FIG. 1 shows a building that constitutes an enclosed airspace that is a gathering area for people.

Referring now to the drawings and in particular to FIG. 1, an enclosed airspace that is a gathering area for people is shown in the form of a building 1. The enclosed airspace could be a subway, airport, entertainment center, religious center, office complex, convention center, or other site where the public is at high risk of exposure to a covert release of biological or chemical agent. The building's roof 2, walls 3, and window and doors 4 form the enclosed airspace. The building is equipped with a heating and air-conditioning system that circulates an air stream within the building. The system of the present invention can be installed in the enclosed airspace, building 1, and in a preferred embodiment can utilize the existing heating and air-conditioning system.

In a terrorist attack, chemical weapons or biological pathogens might be dispersed through release of the agents through sprays into an enclosed airspace. As previously described, there are concerns about environmental safety and medical safety inside an enclosed airspace that are solved by the present invention. Conceptually, the safety of the occupants of a building could be assured by installing a system, such as that described in the Condit et al patent, within the air circulation system of a building. The system would be operated upon detection of a dangerous chemical or biological agent. U. S. Pat. No. 5,938,823, to David A. Condit, Timothy N. Obee, Willard H. Sutton, Richard R. Grzybowski, Christopher M. Pater, Antonio Rinaldi, Sunita Satyapal, Wayde R. Schmidt, Charles R. Winston, and Michael Winter, assigned to Carrier Corporation, filed Apr. 18, 1997, and issued Aug. 17, 1999, is incorporated herein by reference.

The vast majority of buildings need not resort to such an expensive, maintenance-intensive approach, since most buildings will never be the target of a BW agent attack. Following the basic concept of a smoke detector, the present invention minimizes the maintenance burden to a building. That is, the HVAC system would operate essentially unchanged once the new system is installed, except that the new system could activate a precipitator/scrubber if a pathogen were detected in the air supply. Absent this detection, the annual maintenance burden would be only slightly increased.

The public health consequences of a release of biological and chemical agents could be overwhelming. If kilograms of an agent like anthrax were disseminated in New York City today, conservative estimates put the number deaths occurring in the first few days at 400,000. Thousands of others would be at risk of dying within several days if proper antibiotics and vaccination were not started immediately. Millions of others would be fearful of being exposed and seek or demand medical care as well. Beyond the immediate health implications of such an act, the potential panic and civil unrest created would require an equally large response. Local law enforcement agencies would be overwhelmed and would need the assistance of state and federal agencies. The complete vulnerability of public areas such as subways, airports, entertainment centers, religious centers, office complexes, convention centers to this type of terrorism would prompt other terrorists to attempt the same type of attack for extortion or additional terror impact.

Such an attack, the equivalent of a 100-M ton nuclear weapon attack, could be dealt with to some degree if buildings possessed a system such as described and claimed in this patent application. If people were told to stay inside the building while the cloud of BW agent dispersed, and the scrubber was activated, the occupants of the building would be protected until the main cloud of BW agent passed.

In addition, the problem of biological warfare cannot be narrowly baa; focused on its ability to kill or render people ill. Biological warfare's potential to create significant economic loss and subsequent political instability with plausible denial exceeds any other known weapon. Germ warfare at the end of the twentieth and inception of the twenty-first century directly threatens the security of the United States and the achievement of a peaceful, prosperous, and stable post-cold war era.

Figure 2:
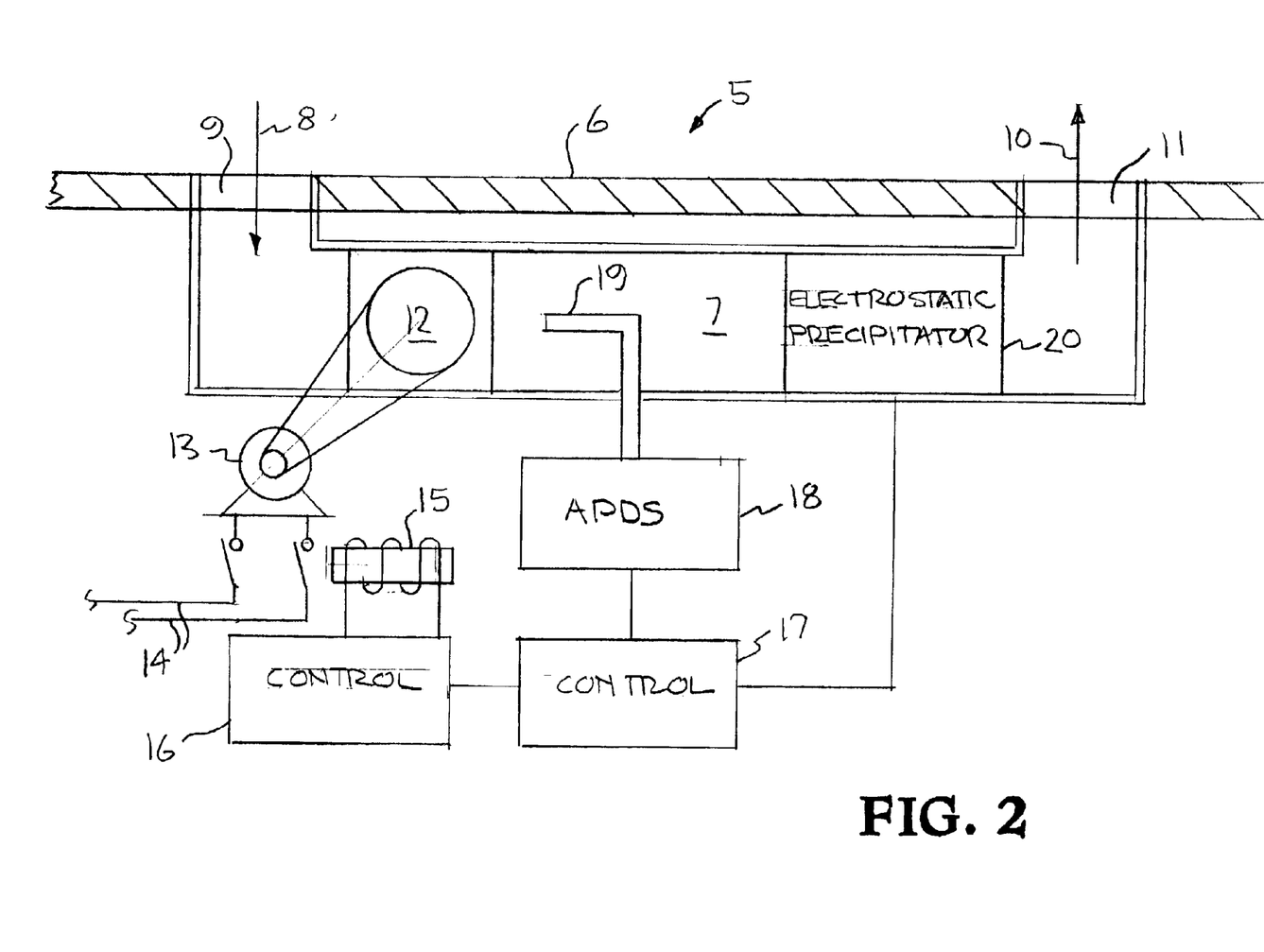
FIG. 2 illustrates an embodiment of a system for the detection and treatment of chemical and biological agents constructed in accordance with the present invention.

Referring now to FIG. 2, an embodiment of the present invention for detecting and remediating biological and chemical agents is illustrated. The system of the present invention could be installed in subways, major office complexes, convention centers, or other sites where the public is at high risk of exposure to a covert release of biological or chemical agents. The system, generally designated by the reference numeral 5, is constructed in accordance with the present invention and provides an autonomous chemical or pathogen detection and remediation system. The system 5 detects and treats unwanted agents within the air inside of an enclosed airspace that is a gathering area for people. The system 5 could be installed in the building 1 shown in FIG. 1. The system 5 is a simple uncomplicated system and is used to illustrate the present invention. The invention can, however, be part of highly complex network of buildings and systems.

The risk posed by chemical agents has two components: a vapor and liquid hazard. Airborne chemical agents can be contacted by humans through inhalation or dermis absorption. An array of chemical point detectors and alarms that can provide real time warnings of exposure are available. In contrast, the hazard posed by airborne biological agents is primarily an inhalation one. The most effective means of delivering a biological agent is via an aerosol in the one-to-five $\mu$m particle size. Creation of this type of an invisible aerosol cloud could be efficiently accomplished using a sprayer, as was demonstrated by the US Official BW program that was unilaterally terminated in the 1960s.

Chemical and toxin attacks can have immediate effect. Pathogen detectors for human respiration need to focus on the following considerations. A calculated respiratory exchange rate, assuming 15% aerobic efficiency, when burning approximately 100 calories/hour with $$n\ O_2+(C(H_2O))_n \rightarrow n\ CO_2+n\ H_2O$$

is 10 liters of air/minute. Starting with 1 ACPLA of B.a., where one particle can be assumed to consist of 15 spores, then a person, assuming high efficiency for deposition and germination of spores in the lungs, would receive a lethal dose of 8000 to 10,000 spores in roughly 1 hour. The respiratory exchange rate can be considered to be higher, 15 liters of air/minute, when you include the sinus cavity, throat, trachea, larynx, mouth, etc.

As shown in FIG. 2, the air within the building is channeled into an air stream 8. This can be accomplished using the building's heating and air-conditioning system. The air flow 8 enters the heating and air-conditioning duct 7 through register 9. The fan 12 moves the air stream through the duct 7. Fan 12 is driven by motor 13. Power for motor 13 is provided by the power source 14. The motor 13 is operated by control 16 that energizes the switching system 15.

Figure 3:
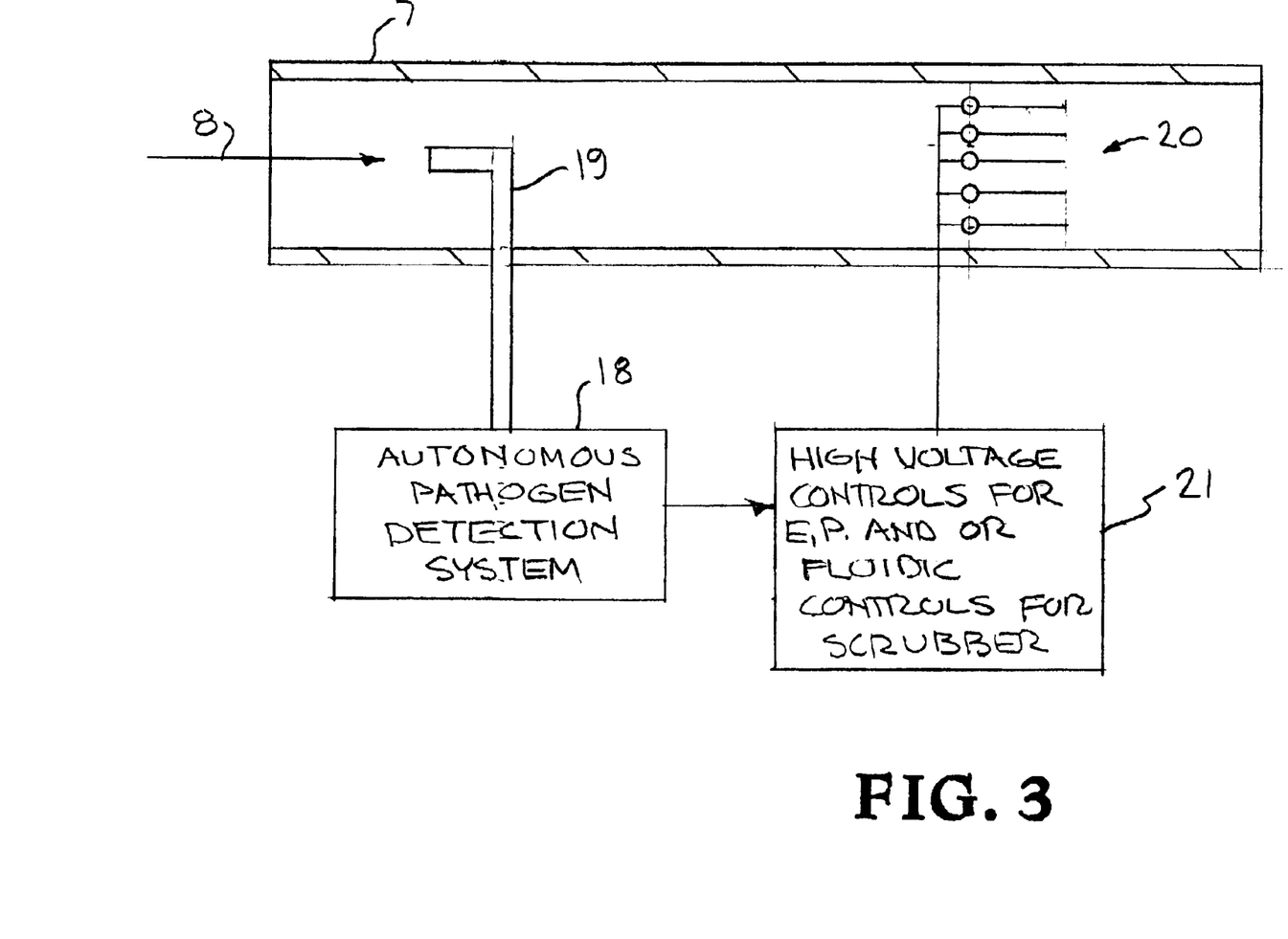
FIG. 3 illustrates the autonomous chemical and pathogen detector and electrostatic precipitator of the system for the detection and elimination of chemical and biological agents constructed in accordance with the present invention.

Referring now to FIGS. 2 and 3, the system for detecting and treating unwanted agents will be described. A chemical/Autonomous Pathogen Detection System (APDS) 18 is connected to the duct 7 through conduit 19. The APDS can be a system that utilizes immunoassays, such as antibody based or synthetic-peptide based immunoassays. The APDS can be a system that utilizes nucleic-acid-based assays, such as the polymerase chain reaction. The APDS can be a system that utilizes mass-spectrometric-based assays. Alternatively, the APDS can be a system that uses a plurality of assays, such as those described above. The system can indude chemical detectors which are well known and commercially available.

A continuous sample of the air stream is channeled to APDS 18 through conduit 19. The APDS 18 is located within the air stream for detecting the unwanted agents. The APDS 18 is connected to a electrostatic precipitator/scrubber 21.

The electrostatic precipitator/scrubber 21 can be a system that traps the airborne threat using electrostatic precipitation. The electrostatic precipitator/scrubber 21 can be a system that uses an aqueous-based spray/aerosol scrubbing system. Alternatively, the electrostatic precipitator/scrubber 21 can be a system that uses both electrostatic precipitation and an aqueous-based spray/aerosol scrubbing system.

Upon detection of an unwanted agent the autonomous chemical and pathogen detector 18 provides a signal to electrostatic precipitator/scrubber 21. The precipitator/scrubber coils 20 inside of air duct are energized to treat the chemical or biological agent. The electrostatic precipitator/scrubber 21 could be a system such as that described in U.S. Pat. No. 5,938,823, to David A. Condit, Timothy N. Obee, Willard H. Sutton, Richard R. Grzybowski, Christopher M. Pater, Antonio Rinaldi, Sunita Satyapal, Wayde R. Schmidt, Charles R. Winston, and Michael Winter, assigned to Carrier Corporation, filed Apr. 18, 1997, and issued Aug. 17, 1999, incorporated herein by reference.

Figure 4:
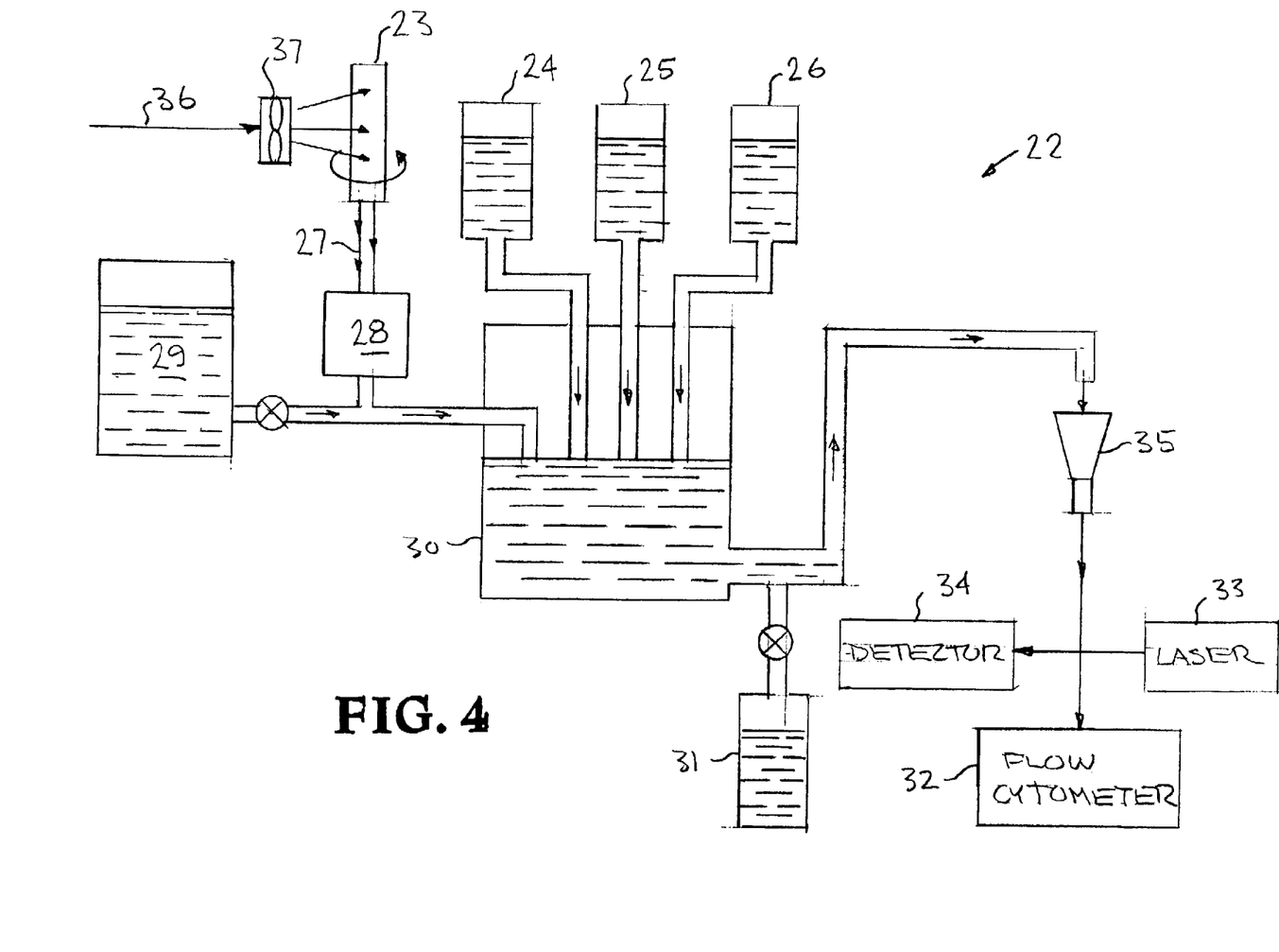
FIG. 4 is a flow diagram of a APDS used in the preferred embodiment of the present invention.

Referring now to FIG. 4, a Autonomous Pathogen Detection System (APDS) used in the preferred embodiment of the present invention is illustrated by a flow diagram. The APDS 18 could be any of the chemical and pathogen detection systems available. The specifications of a APDS 18 used in the preferred embodiment of the present invention indude the following:

Sensitivity: 1 Agent-Containing Particle/Liter of Air, or 1 ACPLA.

Target Pathogens: All agents on the DOD Threat List.

Response Time: 5 min. for surface-recognition ID assay, 20 min. for nucleic-acid-based ID assay.

False-Alarm Rate: less than one per year.

Cycle time: running continuously, 30 min. or less per cycle—adjustable.

Maintenance Schedule: 7 days unattended, or longer.

The APDS, identified generally by the reference numeral 22, includes aerosol collector 23, a system for capture of antibody coated beads 24, a biotin labeled antibody system 25, a fluorescent labeled streptavidin system 26, a flow controller 35, a detector 34, a laser 33, and a flow cytometer 32. The objective is to combine the ultrahigh sensitivity and selectivity of PCR-based biodetection of biological agents with the more general assays that can be performed with flow cytometry. Flow cytometry (FCM) is a technique used to characterize and categorize biological cells and/or their contents, such as DNA, to record their distributions, and can also be used to sort biological material. The biological cells are present in an aqueous-based solution, even when the sample material is eluted from a matrix, such as in sheath-flow detection in electrophoresis experiments. The APDS may operate using a hybrid instrument that employs both antibody based assays and PCR assays.

The flow cytometer 32 provides information for the APDS 22. In flow cytometry, the FCM directs one or more beams of light at the biological material in the aqueous stream and observes the scattered light. The inelastically scattered light which is of interest is usually just fluorescence from an intentionally-included fluorescent molecule, while the elastically-scattered light provides information regarding the size and internal nature of the biological material itself. The small-angle-scattered light, known as "forward-scattered light," serves as a particle-size monitor, while right-angle-scattered (perpendicular-light-scatter, or PLS) light provides a convolution of size and internal structure. In general, less PLS is produced than forward-scattered light, so that it is desirable to collect as much of the PLS as possible in order to maximize the speed and sensitivity of the procedure. U.S. Pat. No. 5,475,487, issued 12 Dec. 1995, to R. P. Mariefla Jr., M. Allen Northrup, G. van den Engh, incorporated herein by reference describes a system that can be used within the system 22.

In previously used flow cytometers, the PLS has been viewed externally to the liquid flow, typically using a high numerical aperture (NA) microscope objective lens or fiber optic. Some of the difficulties associated with this approach are the very limited depth of focus of high-NA optics, and the necessity to align precisely the exact focal point of the lens with the point where the excitation light source intersects the sample flow stream. A significance of the present system is the use of the unconfined aqueous flow stream itself as an optical waveguide. There is no "focal point" for this configuration. Alignment simply requires centering the light source on the flow stream; the liquid optical waveguide is then automatically "aligned". This approach provides inexpensive, high-performance, robust, stable light collection. For the collection of elastically-scattered light, another advantage accrues—the background level of scattered light is extremely low when using this flow-stream waveguide (FSW)—no obscuration bar is needed for the collection of PLS or fluorescence. Several flow cytometers have been built using this principle and have observed lower background noise due to less sensitivity to reflected light in the flow chamber, higher optical throughput, higher accuracy in the measurement, and easier alignment than is available in the lens-based system.

A portable mini flow cytometer, miniFlo, has been built based on the patented in-stream technique for light collection, and it was successfully tested at Dugway during the Joint Field Trials III. All unknowns containing bacterial spores were correctly detected, identified and quantified from $10^3$ spores/ml. through $10^6$ spores/ml. There were no false positives from blank solutions. Flow cytometry (FCM) can be used in a fluorescent Ab-based assay which is much more powerful, more sensitive, and more accurate than any of the Ab-only assays, because multiple physical parameters are measured simultaneously in FCM. The FLS (which gives particle size), PLS (which gives a convolution of particle size and granularity) and fluorescence (the same fluorescence that might be observed in an Ab-only assay) at one or more wavelengths can be collected. Also, since new Ab solution is continuously being provided to the incoming sample, a earlier exposure to sticky substances does not lead to false negatives. The trade-off is, of course, that the instrumentation is more expensive, more difficult to operate, and the resulting data are more difficult to interpret than data from Smart Tickets® or fiber optic probes.

The flow cell cytometer 32 can also be a system such as that disclosed and claimed in U.S. patent application Ser. No. 09/027764, filed Feb. 23, 1998, by Raymond P. Maijella Jr. for Waveguide Detection of Right-Angle-Scattered Light In Flow Cytometry, which is incorporated herein by reference. That system uses a transparent flow cell as an index-guided optical waveguide, similar in some respects to U.S. Pat. No. 5,475,487. A detector for the flow cell but not the liquid stream would then be used to detect the Right-Angle-Scattered (RAS) Light, (RAS includes both PLS and inellastically-scattered light), exiting from one end of the flow cell. As before, the detector(s) could view the trapped RAS light from the flow cell either directly or through intermediate optical light guides. If the light exits the end of the flow cell referred to as "bottom," then the top of the flow cell could be given a high-reflectivity coating to approximately double the amount of light collected. This system would be much more robust in its alignment than the traditional flow cytometry systems which use imaging optics, such as microscope objectives.

This system passes the liquid stream of a flow cytometer through a flow cell which is transparent to both the excitation light and the scattered light, including elastically scattered light and/or inelastically scattered light, as appropriate. A transparent flow cell is used as an index-guided optical waveguide, similar in some respects to U.S. Pat. No. 5,475, 487, except that the cell is fabricated from a transparent material whose index of refraction at the scattered wavelengths is larger than that of the liquid stream and the air, as well. I.e., for a (typical) aqueous stream with n=1.33, quartz or glass with n=1.4 could be employed. A detector for the flow cell but not the liquid stream would then be used to detect the RAS light exiting from one or both ends of the flow cell. As before, the detector(s) could view the trapped RAS light from the flow cell either directly or through intermediate optical light guides.

A basic embodiment of the system utilizes a transparent flow cell with a hollow flow capillary. The transparent flow cell may include a high-reflection coating on one end, and may further include an anti-reflection coating on the other end. A detector having a hole is coupled to the end. In operation, cells, chromosomes, or other types of particulate suspended in a liquid flow through the hollow flow capillary in the transparent flow cell, and through the hole in detector to form droplets. As the particulate passes through the flow cell, a laser beam from a laser is directed through the transparent flow cell, where it interacts with the particulate to produce, inter alia, scattered light. This scattered light can propagate onto detector in three ways: (i) by a direct path as e.g., (ii) by reflection from the high-reflection coating on end and subsequent waveguide transmission from the walls of the flow cell, or (iii) by waveguide transmission from the walls of the flow cell.

Any light trapped within the liquid stream is lost. Since the amount of confined light, roughly approximately equal to the area multiplied by the index of refraction, tends to be confined within the material with the higher index of refraction, and if the area of the flow cell (in the plane which is perpendicular to the flow direction) supports one or more index-guided waveguide modes, is much greater than the cross section of the flow stream, then very little light will be lost to the flow stream. Another advantage of this design is that the top end of the flow cell can be coated with a material that presents high reflectivity (HR) to the RAS which travels away from the detector. This HR material could either be metal or a broadband multilayer reflector, for example. The broadbanded nature of the detector is needed because the trapped RAS light, even if monochromatic, would strike the end at a variety of angles. Similarly, the exit face of the flow cell could be anti-reflection coated to increase the transmission of RAS light to the detector and, hence, the overall efficiency of the system.

Another basic embodiment of the invention, which utilizes a transparent flow cell with a hollow flow capillary. The transparent flow cell make a right angle such that fluid exits the flow cell at approximately a right angle, and light continues to travel straight. The right angle bend in the liquid flow channel separates the liquid from the light guiding. The cell may include a high-reflection coating on one end, and may further include an anti-reflection coating on the other end. A detector is coupled to the end. In operation, cells, chromosomes, or other types of particulate suspended in a liquid flow through the hollow flow capillary in the transparent flow cell to flow out of the system. As the particulate passes through the flow cell, a laser beam from a laser is directed through the transparent flow cell, where it interacts with the particulate to produce, inter alia, scattered light. Note that the orientation of the flow cell direction of flow is not relevant, which enables sorting or debubbling. This scattered light can propagate onto detector in the same three ways as described. Additionally, some of the light trapped within the flow stream would be detected due to coupling from the hollow flow capillary 112. As the flow capillary approaches a right angle, there exists an angle after which the flow capillary does not exceed the critical angle, and TIR is lost. Some light is lost due to the blocking effect of the right angle made by the flow capillary as it exits the flow cell.

A third embodiment utilizes a transparent flow cell with a hollow flow capillary. This embodiment the element of a reflecting surface, embedded within the flow cell in the liquid flow channel to guide the induced scatter onto a photodetector. As cells flow by, they generate scatter in the laser beam. Some of this scatter reflects toward the high-reflective surface, and some of this light reflects from high-reflective surface to exit the system onto a photodetector. This embodiment may also include a high reflecting surface 218 at the exit of the flow cell. All of the light trapped within the flow stream would be lost.

The APDS system 22 provides a collector running with 200 l/min air throughput at 50% collection efficiency of the spore particles, collection over a period of 2 minutes into a volume of 1 ml of water would provide $2 \times 10^2$ particles/ml/ ACPLA. If the fluidics that prepares the collected sample performed at 70% efficiency, then, starting with an aerosol of 1 ACPLA of spore particles, the aqueous concentration of spores for the assays would be roughly $2 \times 10^3$ spores/ml, a level already demonstrated for detection, identification, and quantification by the miniFlo Ab-based assay during JFT III. One particle consists of a dump of roughly 15 spores.

Referring again to FIG. 4 the air stream circulation system including fan 37 that moves air within the air stream. The air stream will contain pathogens 36 in the case of a terrorist attack. The aerosol collector provides a sample 27 which is conveyed to a fractional pre concentrator 28. The flow cytometer will provide a signal upon the detection of the pathogens 36. This signal is transmitted to the controller. The controller activates the electrostatic precipitator/ scrubber in response to detection of the pathogens 36. The cleaning fluid 29 can be used to circulate through the system for servicing. The cleaning fluid 29 is disposed of through waste 31.

This system can be used to monitor and remediate the air inside of an enclosed airspace that is a gathering area for people. This could be an office building, an event center, public transportation or other contained airspace. Examples of areas that need protection are subways, airports, entertainment centers, religious centers, office complexes, convention centers, and other sites where the public is at high risk of exposure to a covert release of biological or chemical agents. The system could be used for the detection and treatment of chemical and biological agents in the event a terrorist were to release an aerosolized pathogen into the airspace or the ventilation system. The present invention provides a prophylactic approach that can avoid many of the problems of the prior art by providing a filter of all of the air supply.

One reason bioweapons are considered likely for use in terrorist attacks is to their low production costs, the easy access to a wide range of disease-producing biological agents, their non-detection by routine security systems, and their easy transportation from one location to another. Their properties of invisibility and virtual weightlessness render detection and verification procedures difficult and make non-proliferation of such weapons virtually impossible.

Biological agents are many times deadlier, pound-for pound, than chemical agents. One gram of anthrax spores could kill as many people as a ton of the nerve agent sarin. There are four distinct types of chemical weapons: nerve, blister, blood, and incapacitating agents. The effects from these chemical agents can occur within seconds of exposure as in the case of nerve and blood agents or as long as several hours in the circumstance of low-dose blister agent exposure such as mustard gas.

Of the four general types of biological warfare agents mentioned, 60 have been identified with potential weapon utility against humans. The medical effects of biological agents are diverse and are not necessarily related to the type of agent. Some cause pneumonia. Others can cause encephalitis or inflammation of the brain. Each one causes a different complex of symptoms, which can either incapacitate or kill its victim.

The effective dose required to induce illness or death may be as great as tens of thousand of organisms as in the case of anthrax or just a few as with tularemia. With the exception of exposure to a toxin, a period of several days or even weeks may pass before the onset of symptoms and the ultimate effect. This incubation period is the time necessary for the microbe or viral agent to establish itself in the host and replicate.

Toxins, on the other hand, are a product of living organisms and behave similar to chemical agents. Botulism toxin is the most toxic substance known to man. Without supportive care, inhalation of nanograms (10–9 grams) of this agent will cause progressive muscular paralysis leading to asphyxiation and death.

There are other uses of the present invention. Air monitoring is of critical importance to public health assessment. There needs to be a system capable of providing a warning of high level of airborne particulates and of the dangerous particulates. Recirculation of air in buildings as indoor pollution causes worker illness. Nosocornial, or hospital-acquired infections, are often caused by antibiotic resistant microorganisms spread throughout the hospital in air-handling systems. The infections are also in the ambient air caused by movement between rooms by hospital personnel.

The autonomous chemical and pathogen detector and electrostatic precipitator/scrubber of the present invention provides a system for the detection and treatment of chemical and biological agents. The electrostatic precipitator/scrubber is installed downstream of the Autonomous Pathogen Detection System (APDS). Upon first warning the electrostatic precipitator or scrubber is switched on. When not activated, the electrostatic precipitator or scrubber will present very little constriction to the overall airflow in the heating and air-conditioning system of the building. The maintenance costs will be minimal. For example, perhaps once per year the accumulated deposits might need to be washed off.

Moreover, the electrostatic precipitator/spray scrubber and autonomous chemical and pathogen detector combination would have a fail-safe property. The electrostatic precipitator/spray scrubber is connected to the same electrical circuit as the blower/fan on the heating and air-conditioning system. In the event the electricity failed on the electrostatic precipitator/spray scrubber or the electrostatic precipitator/spray scrubber experienced other failure so that it could not trap the pathogen, the blower/fan would not be pushing the pathogen toward people in the enclosed airspace in building. The system of the present invention has the added feature that it will archive a sample for later analysis.

While particular embodiments, operational sequences for fabrication, materials, parameters, etc., have been set forth to exemplify and explain the principles of the invention, such are not intended to be limiting. Modifications and changes may become apparent to those skilled in the art, and it is intended that the invention be limited only by the scope of the appended claims.

What is claimed is:

1. A method for protecting an enclosure against chemical weapons and/or biological pathogens by the detection of said chemical weapons and/or biological pathogens and by the treatment of said chemical weapons and/or biological pathogens agents within the air inside of an enclosed airspace that is a gathering area for people, the air circulated in an air stream, comprising:

circulating said air within said air stream, detecting said chemical weapons and/or biological pathogens agents, generating a signal upon detection of said chemical weapons and/or biological pathogens agents, and using said signal to activate a treatment system connected to said air stream for treating said chemical weapons and/or biological pathogens agents, said treatment system treating said air within said air stream.

2. The method of claim 1, including the step of stopping said circulation system if said treatment system shuts down.

3. An apparatus that detects the presence of airborne chemical weapons and/or biological pathogens threats to the human occupants of an enclosed airspace that is served by a forced-air circulation system and treats said chemical weapons and/or biological pathogens threats, said forced-air circulation system circulating an air stream, comprising:

an autonomous chemical and pathogen detector within the said forced-air circulation system that detects the presence of airborne chemical weapons and/or biological pathogens threats, a treatment system for treating said chemical weapons and/or biological pathogens threats, said treatment system treating said air stream, and a control, responsive to said autonomous chemical and pathogen detector, for activating said treatment system in response to detection of said chemical weapons and/or biological pathogens agents.

4. An apparatus that detects, identifies, and quantifies the presence of airborne chemical weapons and/or biological pathogens threats to the human occupants of an enclosed airspace that is served by a forced-air circulation system and treats said airborne chemical weapons and/or biological pathogens threats, said forced-air circulation system circulating an air stream, comprising:

an autonomous chemical and/or pathogen detector within the said forced-air circulation system that detects, identifies, and quantifies the presence of airborne chemical weapons and/or biological pathogens threats, a treatment system for treating said chemical weapons and/or biological pathogens threats, said treatment system treating said air stream, and a control, responsive to said autonomous chemical and/or pathogen detector, for activating said treatment system in response to detection of said chemical weapons and/or biological pathogens agents.

5. The apparatus of claim 4 wherein said autonomous chemical and pathogen detector utilizes immunoassays and said immunoassays include antibody based or synthetic-peptide based immunoassays.

6. The apparatus of claim 4 wherein said autonomous chemical and pathogen detector utilizes nucleic-acid-based assays and said nucleic-acid-based assays include the polymerase chain reaction.

7. The apparatus of claim 4 wherein said autonomous chemical and/or pathogen detector utilizes mass-spectrometric-based assays.

8. The apparatus of claim 4 wherein said autonomous chemical and pathogen detector utilizes a plurality of assays and said plurality of assays include antibody based or synthetic-peptide based immunoassays, nucleic-acid-based assays and said antibody based or synthetic-peptide based immunoassays, nucleic-acid-based assays include the polymerase chain reaction immunoassays, and mass-spectrometric-based assays.

9. The apparatus of claim 4 wherein said treatment system utilizes an electrostatic precipitator.

10. The apparatus of claim 4 wherein said treatment system utilizes an aqueous-based spray/aerosol scrubbing system.

11. The apparatus of claim 4 wherein said treatment system utilizes both electrostatic precipitation and an aqueous-based spray/aersol scrubbing system.

* * * * *